United States Patent [19]

Rusch

[11] Patent Number: 4,613,354
[45] Date of Patent: Sep. 23, 1986

[54] COMPOSITION FOR DEFOLIATING PLANTS

[75] Inventor: Reinhart Rusch, Berlin, Fed. Rep. of Germany

[73] Assignee: Schering Aktiengesellschaft, Berlin and Bergkamen, Fed. Rep. of Germany

[21] Appl. No.: 503,725

[22] Filed: Jun. 13, 1983

[30] Foreign Application Priority Data

Jun. 11, 1982 [DE] Fed. Rep. of Germany ....... 3222622

[51] Int. Cl.$^4$ ............................................. A01N 43/82
[52] U.S. Cl. ........................................... 71/73; 71/70; 71/90; 71/120; 71/83; 71/87; 71/88; 71/91; 71/92; 71/94; 71/95
[58] Field of Search ......................... 71/70, 73, 90, 120

[56] References Cited

U.S. PATENT DOCUMENTS 4,294,605 10/1981 Arndt et al. ........................ 71/73

FOREIGN PATENT DOCUMENTS 0059011 2/1982 European Pat. Off. .
472488 10/1975 U.S.S.R. .

OTHER PUBLICATIONS

Ger. Offen. 2,745,968, Chem. Abst. vol. 91 (1979).

Primary Examiner—Catherine L. Mills
Attorney, Agent, or Firm—Michael J. Striker

[57] ABSTRACT

New compositions for defoliating plants possessed of synergistic activity comprising (A) a compound of formula I

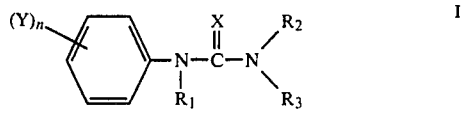

in which
$R_1$ is hydrogen or $C_1$–$C_4$-alkyl,
$R_2$ is hydrogen, $C_1$–$C_4$-alkyl, $C_1$–$C_4$-alkoxy or $C_1$–$C_4$-alkylthio,
$R_3$ is hydrogen, $C_1$–$C_4$-alkyl, $C_1$–$C_4$-alkoxy, $C_1$–$C_4$-alkylthio or $C_3$–$C_8$-cycloalkyl,
wherein $R_2$ and $R_3$ taken together with the nitrogen atom to which they are attached is a morpholino-piperidino- or pyrrolidino-group,
X is oxygen or sulfur,
Y can be the same or different and is hydrogen, halogen, $C_1$–$C_4$-alkyl, $C_1$–$C_4$-alkoxy, $C_1$–$C_4$-alkoxy-$C_1$–$C_2$-alkyl, $C_1$–$C_4$-alkylthio, trifluoromethyl or nitro, and
n is the number 1, 2, 3, 4 or 5, in combination with
(B) a defoliant for plants
in a proportion of 1 to 99 parts by weight of component (A) to 99 to 1 parts by weight of component (B).

As the defoliant there can be employed 1,2,3-thiadiazole-5-yl-urea derivatives, 1,2,3-thiadiazole-5-carboxylic acid derivatives, benzylaminopurine derivatives, 2,3-dihydro-5,6-dimethyl-1,4-dithiine-1,1,4,4-tetroxide, 1,1'-dimethyl-4,4'-bipyridilium-dichloride, sodium chlorate and S,S,S-tributylphosphortrithioate.

The compositions of the invention are especially suitable for use in the defoliation of cotton plants.

15 Claims, No Drawings

COMPOSITION FOR DEFOLIATING PLANTS

BACKGROUND OF THE INVENTION

This invention relates to new compositions for defoliation of plants, which compositions are characterized by synergistic activity.

The new compositions contain as essential ingredients two components which in their combined use mutually influence each other and together exert a biological effect or activity which is greater than the sum of the activities of the individual components. Such effect can be identified as a synergistic effect. This synergistic activity in the case of the compositions of the invention results in an increase in the formation of abscission layer in the plant and results in a regulated repelling or sloughing off of the leaf stems and the leaves of the treated plants.

Agents for defoliating plants are already known and have been described for example in DE-OS No. 25 06 690; DE-OS No. 26 19 861; U.S. Pat. No. 2,954,467, for example. It is already known that certain mixtures of these agents display a synergistic effect. (DE-OS No. 26 46 712; DE-OS No. 27 45 968). Such compositions have been inadequate in that the defoliation is incomplete and in that secondary effects of an undesirable nature are produced. Thus there exists a need for more effective compositions and agents having such increased activity which can be used in reduced amounts for avoiding unnecessary injury to the plants and to the environment.

SUMMARY OF THE INVENTION

The present invention has as its object the provision of compositions and methods for defoliating plants having synergistic activity.

Another object of the present invention is the provision of compositions and methods for having synergistic activity for preparing agricultural crops for harvest.

Still further objects will be apparent from the further description of the invention hereinafter.

These objects are achieved by providing new defoliant compositions and applying them to the plants in which it is desired to produce defoliation. The compositions of the invention comprise
(a) a compound of formula I

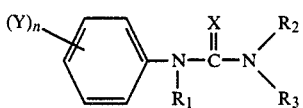

in which
$R_1$ is hydrogen or $C_1$-$C_4$—alkyl,
$R_2$ is hydrogen, $C_1$-$C_4$—alkyl, $C_1$-$C_4$—alkoxy or $C_1$-$C_4$—alkylthio,
$R_3$ is hydrogen, $C_1$-$C_4$—alkyl, $C_1$-$C_4$—alkoxy, $C_1$-$C_4$—alkylthio or $C_3$-$C_8$—cycloalkyl, wherein
$R_2$ and $R_3$ taken together with the nitrogen atom to which they are attached is a morpholino-, piperidino- or pyrrolidino-group,
X is oxygen or sulfur,
Y is the same or different and is hydrogen, halogen, $C_1$-$C_4$—alkyl, $C_1$-$C_4$—alkoxy, $C_1$-$C_4$—alkoxy—$C_1$-$C_2$—alkyl, $C_1$-$C_4$—alkylthio, trifluoromethyl or nitro, and
n is the number 1, 2, 3, 4, or 5,
in combination with (B) a defoliant for plants
in a proportion of 1 to 99 parts by weight of component (A) to 99 to 1 parts by weight of component (B).

The aforesaid compositions surprisingly have a growth regulating effect which is higher than the sum of the effects of either of the individual components. The compositions produce a synergistic effect and that to a degree which was not to have been expected.

The state of the art is as a result of the few compositions of the invention substantially advanced.

Cotton compounds of Formula I (component A) when used alone have no defoliant activity on the plants, so that their use in the synergistic mixtures for defoliation of cotton plants in accordance with the invention provides a new use for such compounds.

The technical advance of the compositions of the invention is realized therefore not only in the activity increase over the not always satisfactory defoliation agents heretofore available, but also in the technical utilization of a class of compounds heretofore not considered in connection with any plant growth regulating activity with respect to cotton plants.

As compounds of Formula I (component A) there are suitable in particular compositions wherein
$R_1$ is hydrogen, methyl or ethyl,
$R_2$ is hydrogen, methyl, methoxy or methylmercapto,
$R_3$ is hydrogen, methyl, ethyl, propyl, butyl, methoxy, methylmercapto, cyclopropyl, cyclopentyl, cyclohexyl or methylcyclohexyl, or
$R_2$ and $R_3$ taken together with the Nitrogen atom to which they are attached is a morpholino-, piperidino- or pyrrolidino-group,
X is oxygen or sulfur,
Y is the same or different and is hydrogen, chlorine, bromine, fluorine, methyl, ethyl, propyl, isopropyl, butyl, methoxy, methylmercapto, trifluoromethyl or nitro, and
n is the number 1, 2, 3, 4 or 5.

Especially suitable for the purposes of the invention are the following compounds:
N-(3,4-dichlorophenyl)-N',N'-dimethyl urea,
N-(4-chlorophenyl)-N',N'-dimethyl urea,
N-phenyl-urea,
N-(4-isopropylphenyl)-N',N'-dimethyl urea,
N-(3-trifluoromethylphenyl)-N',N'-dimethyl urea,
N-(3-chloro-4-methyl-phenyl)-N',N'-dimethyl urea
N-(3-chloro-4-methoxy-phenyl)-N',N'-dimethyl urea,
N-(4-bromo-phenyl)-N'-methoxy-N'-metthyl urea,
N-(3,4-dichloro-phenyl)-N'-methoxy-N'-methyl urea,
N-(4-chlorophenyl)-N'-methoxy-N'-methyl urea,
N-phenyl-N',N'-dimethyl urea, and
N-(3,4-dichlorophenyl)-N'-methyl-N'-n-butyl urea.

These compounds are already known and can be prepared according to the known methods.

As defoliants (component B) there are suitable in accordance with the invention also heretofore known compounds with known defoliant activity. As preferred instances of compounds of this class there can be mentioned:
1,2,3-thiadiazole-5-yl urea derivatives,
1,2,3-thiadiazole-5-carboxylic acid derivatives,
benzylaminopurine derivatives,
2,3-dihydro-5,6-dimethyl-1,4-dithiine-1,1,4,4-tetroxide,
1,1'-dimethyl-4,4'-bipyridilium-dichloride,
sodium chlorate, and
S,S,S-tributylphosphortrithioate.

As 1,2,3-thiadiazole-5-yl-urea derivatives there are especially suitable compounds having the formula II

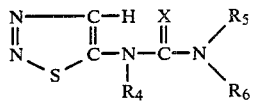

wherein
R₄ is hydrogen or $C_1$-$C_3$—alkyl,
R₅ is hydrogen or $C_1$-$C_4$—alkyl,
R₆ is $C_1$-$C_4$—alkyl, $C_3$-$C_8$—cycloalkyl, phenyl, halogenophenyl, methylphenyl, methoxyphenyl, nitrophenyl or pyridyl, and
X is oxygen or sulfur.

Particularly preferred are the following compounds:
1-phenyl-3-(1,2,3-thiadiazole-5-yl)-urea,
1-methyl-1-phenyl-3-(1,2,3-thiradiazol-5-yl)-urea,
1-(2-methylphenyl)-3-(1,2,3-thiadiazole-5-yl)-urea, or
1-(2-pyridyl)-3-(1,2,3-thiadiazole-5-yl)-urea.

In accordance with the invention it has been found that as defoliant component B the following compounds are especially suitable, i.e. as the 1,2,3-thiadiazole-5-carboxylic acid derivatives: 4-methyl-1,2,3-thiadiazole-5-carboxylic acid-(cyclohexylmethylamide) and as the benzyl aminopurine derivative d(+)-6(α-methylbenzylaminopurine).

The synergistic activity of the composition that is of the mixture of the invention is significantly evident when the weight ratio of 1 to 99 weight parts of component A to 99 to 1 weight parts of component B are used, although satisfactory activity is present in ratios which fall above or below those values just indicated.

An optimal increase in activity is shown by compositions wherein there are present 1 to 10 parts by weight of component A and part by weight of defoliant component B.

The weight ratios are to be determined by taking into consideration the sensitivity and resistance of the plants involved, the time of application, the climate conditions, the soil conditions as well, etc. The compositions of the invention are suitable for defoliation of plants and for effecting such defoliation as well and therewith for preparing agricultural crops for harvest, and this is particularly true for cotton plants.

The amounts to be employed in general are 1 to 10,000 g of the mixture (components A and B)/2.5 acres and preferably about 10 to 1,000 g of the mixture/2.5 acres.

The compositions of the invention can be employed in a conventional manner, for example with water as the carrier as for instance in sprays of about 100 to 2000 liters/2.5 acres. The compositions of the invention can also be used in the so-called "low-volume" or "ultra-low-volume-process". Further, the compositions of the invention can also be used in admixture with other active agents, as for example other defoliants, herbicides, plant protection agents or pest control agents, etc.

The nature and rate of the action of a composition may be increased by the addition of various additives such as organic solvents, wetting agents or oils. Their use may furthermore allow for reduction in the amount of the composition or of one or other of the active components thereof.

The compositions of the invention are preferably used in the form of powders, dust formulations, solutions, emulsions or suspensions under suitable addition of liquid and/or solid carrier materials or diluents and, if desired, wetting agents, adhesion promoting agents, emulsifiers and/or dispersants.

Suitable liquid carriers are for example water, aliphatic and aromatic hydrocarbons as for instance benzene, toluene, xylene, cyclohexanone, isophorone, dimethylsulfoxide, dimethylformamide, and various mineral oil fractions.

As solid carrier materials there are suitable for example tonsil, silica gel, talc, kaolin, attaclay, limestone, silicic acid and plant-derived products such as flours.

As surface-active agents which may be included in the compositions, there can be mentioned for example, calcium lignosulfonate, polyoxyethylene-alkyl-phenolether, naphthaline sulfonic acid and its salts, phenolsulfonic acid and its salts, formaldehyde condensation products, fatty alcohol sulfates as well as the substituted benzene sulfonic acids and their salts.

The total amount of the mixture (components A and B) in the composition as used can vary widely. For example, the compositions may include about 10–80% by weight of the active agents, about 90–20% by weight of liquid and/or solid carrier material and, if desired up to 20% by weight of surface-active agents.

The preparation of the compositions of the invention can be for example carried out using the following formulations of ingredients:

(a)
90% mixture (components A+B)
7% kaolin
3% surface-active agents on the basis of the sodium salt of N-methyl-N-oleyl-taurine and the calcium salt of lignin sulfonic acid (b)
50% mixture (components A+B)
35% colloidal silicic acid
10% calcium salt of lignin sulfonic acid
5% ammonium salt of monosulfuric acid ester of tetraethylene-lgycol-nonyl-phenylether (c)
30% mixture (components A+B)
2% calcium salt of lignin sulfonic acid
68% water (d)
20% mixture (components A+B)
70% tonsil
8% cellulose pitch
2% wetting agent on the basis of a fatty acid condensation product (e)
5% mixture (components A+B)
80% tonsil
10% cellulose pitch
5% wetting agent on the basis of a fatty acid condensation product The preparation of the compositions of the invention takes place by mixing together the single components in suitable mixing equipment.

The following examples will further illustrate the invention, but are in no wise to be taken as limitative of the scope thereof.

Cotton plants which were treated in a hothouse at the stage of their development where they have 4–8 opened up deciduous leaves with one of the components or a mixture thereof as well be set out hereinafter.

The amounts of a composition of the invention used in examples are stated in each example. The compositions were applied in the form of their solutions or suspensions in 500 liters of water per about 2.5 acres.

Each active agent has been assigned a Roman numeral for expressing the respective synergistic action of the specific composition.

The effect was evaluated by determining the number of shed leaves in the amount of time indicated after treatment. The results express the defoliation as a percentage of the total number of deciduous leaves present prior to treatment. The results are calculated by counting the number of leaves remaining after the specified time following the application and determining the percentage of the total originally present.

In each test the same number of plants was used, each having a number of leaves in the range indicated. From test to test, the leaf total differed by less than 20-32 foliage leaves. The following reported data contains particulars for the components A and B, including the amounts used as well as the calculated percentage of defoliation for each of components and for the combination thereof.

In addition, in a separate column, the term E was calculated according to the method by S. R. Colby ("Calculating Synergistic and Antagonistic Responses of Herbicide Combinations", Weeds 15/1 (1967), pp. 20–22).

This term E shows the additive effect of the individual components of the composition. Wherever a higher value was observed than the value for E, a truly synergistic effect was present.

The term E was calculated according to the equation:

$$E = X + Y - (XY/100)$$

In these equations, the different symbols used have the following meanings:
X = percentage of defoliant action with a compound A at p kg of active agent per about 2.5 acres;
Y = percentage of defoliant action with a compound B at q kg of active agent per about 2.5 acres;
E = defoliant action expected by use of A plus B at p+q kg/about 2.5 acres.

EXAMPLE 1

Young cotton plants in a stage of development having 5–7 evolved leaves were treated with the following components or their mixtures (four times). The components were used in an amount of water corresponding to 500 liters/2.5 acres. After 2 weeks, the percentage of dropped leaves was determined. The results are set out in the following table:

| Compound | | Amount of compound in g/2.5 acres | Defoliation in % | E (Colby) |
|---|---|---|---|---|
| (B) | | | | |
| N—phenyl-N'—(1,2,3-thiadiazole-5-yl)-urea | = I | 10 | 10 | |
| | | 20 | 14 | |
| | | 40 | 33 | |
| (A) | | | | |
| N—(3,4-dichloro-phenyl)-N',N'—dimethyl-urea | = II | 200 | 0 | |
| N—(4-chloro-phenyl)-N',N'—dimethyl-urea | = III | 200 | 0 | |
| N—phenyl-urea | = IV | 200 | 0 | |
| N—(4-isopropyl-phenyl)-N',N'—dimethyl-urea | = V | 200 | 0 | |
| N—(3-trifluoromethyl-phenyl)—N',N'—dimethyl-urea | = VI | 200 | 0 | |
| N—(3-chloro-4-methyl-phenyl)-N',N'—dimethyl-urea | = VII | 200 | 0 | |
| N—(3-chloro-4-methoxy-phenyl)-N',N'—dimethyl-urea | = VIII | 200 | 0 | |
| N—(4-bromo-phenyl)-N'—methoxy-N'—methyl-urea | = IX | 200 | 0 | |
| N—phenyl-N',N'—dimethyl-urea | = XII | 200 | 0 | |
| I + II | | 10 + 100 | 57 | (10) |
| | | 20 + 100 | 81 | (14) |
| I + III | | 10 + 100 | 65 | (10) |
| | | 20 + 100 | 75 | (14) |
| I + IV | | 20 + 100 | 67 | (14) |
| I + V | | 20 + 100 | 60 | (14) |
| I + VI | | 20 + 100 | 68 | (14) |
| I + VII | | 20 + 100 | 75 | (14) |
| I + VIII | | 20 + 100 | 83 | (14) |
| I + IX | | 20 + 100 | 62 | (14) |
| I + XII | | 20 + 100 | 54 | (14) |

EXAMPLE 2

Young cotton plants having 5–8 evolved leaves were treated as described in Example 1 and the results obtained then evaluated.

| Compound | | Amount of active agent in g/2.5 acres | Defoliation in % | E (Colby) |
|---|---|---|---|---|
| (B) | | | | |
| N—phenyl-N'—(1,2,3-thiadiazole-5-yl)-urea | = I | 20 | 12 | |
| | | 80 | 36 | |
| (A) | | | | |
| N—(3,4-dichloro-phenyl)-N',N'—dimethyl-urea | = II | 200 | 0 | |
| N—(3,4-dichloro-phenyl)-N'—methoxy-N'—methyl-urea | = X | 200 | 0 | |
| N—(4-chlorophenyl)-N'—methoxy-N'—methyl-urea | = XI | 200 | 0 | |
| N—(3,4-dichloro-phenyl)-N'—methyl-N'—n-butyl-urea | = XIII | 200 | 0 | |
| I + II | | 20 + 30 | 72 | (12) |
| I + X | | 20 + 30 | 76 | (12) |
| I + XI | | 20 + 30 | 74 | (12) |
| I + XIII | | 20 + 30 | 43 | (12) |

EXAMPLE 3

Young cotton plants having 4–6 evolved leaves were treated as set out in Example 1 and the results obtained and evaluated.

| Compound | | Amount of active agent in g/2.5 acres | Defoliation in % | E (Colby) |
|---|---|---|---|---|
| (B) | | | | |
| N—phenyl-N'—(1,2,3-thiadiazole-5-yl)-urea | = I | 80 | 32 | |

-continued

| Compound | | Amount of active agent in g/2.5 acres | Defoliation in % | E (Colby) |
|---|---|---|---|---|
| (A) | | | | |
| N—(3,4-dichloro-phenyl)-N',N'—dimethyl-urea | = II | 200 | 0 | |
| | I + II | 40 + 40 | 100 | |

EXAMPLE 4

Young cotton plants having 5-6 evolved leaves were treated as set out in Example 1 and the results obtained were evaluated.

| Compound | | Amount of active agent in g/2.5 acres | Defoliation in % | E (Colby) |
|---|---|---|---|---|
| (B) | | | | |
| N—phenyl-N'—(1,2,3-thiadiazole-5-yl)-urea | = I | 50 | 33 | |
| (A) | | | | |
| N—(3,4-dichloro-phenyl)-N',N'—dimethyl-urea | = II | 500 | 0 | |
| | I + II | 50 + 100 | 95 | (33) |

EXAMPLE 5

Young cotton plants having 4-6 evolved leaves were treated with the compound (four times) as hereinafter set out or with their mixtures. The amount of spray as used was 500 liters/2.5 acres. A few day after the application of the active agent (using active agent I alone, no leaf abscission was observed), the percentages of defoliated leaves were determined. The table clearly shows the increased action velocity of the compositions of the invention.

| Compound | | Amount of active agent in g/2.5 acres | Defoliation in % | E (Colby) |
|---|---|---|---|---|
| (B) | | | | |
| N—phenyl-N'—(1,2,3-thiadiazole-5-yl)-urea | = I | 20 | 0 | |
| | | 160 | 0 | |
| (A) | | | | |
| N—(3,4-dichloro-phenyl)-N',N'—dimethyl-urea | = II | 500 | 0 | |
| | I + II | 100 + 10 | 70 | |
| | | 10 + 400 | 45 | |

EXAMPLE 6

Young cotton plants having 5-7 evolved leaves were treated as described in Example 5 and at about the time of the onset of leaf fall using compound I the results were evaluated.

| Compound | | Amount of active agent in g/2.5 acres | Defoliation in % |
|---|---|---|---|
| (B) | | | |
| N—phenyl-N'—(1,2,3-thiadiazole-5-yl)-urea | = I | 30 | 4 |
| | | 60 | 13 |
| | | 100 | 17 |
| (A) | | | |
| N—(3,4-dichlorophenyl)-N',N'—dimethyl-urea | = II | 100 | 0 |
| N—(4-chlorophenyl)-N',N'—dimethyl-urea | = III | 100 | 0 |
| | I + II | 30 + 15 | 79 |
| | I + III | 30 + 15 | 87 |

EXAMPLE 7

Rooted hibiscus plants having a growth height of 20-30 cm and 8-10 leaves were treated with the following compounds or their mixtures and the results evaluated after 1.5 weeks.

| Compound | | Amount of active agent in g/2.5 acres | Defoliation in % | E (Colby) |
|---|---|---|---|---|
| (B) | | | | |
| N—phenyl-N'—(1,2,3-thiadiazole-5-yl)-urea | = I | 5 | 33 | |
| (A) | | | | |
| N—(3,4-dichloro-phenyl)-N',N'—dimethyl-urea | = II | 50 | 0 | |
| | I + II | 5 + 30 | 41 | (33) |

EXAMPLE 8

Young cotton plants having 4-6 evolved leaves were treated as described in Example 1 and the results evaluated.

| Compound | | Amount of active agent in g/2.5 acres | Defoliation in % |
|---|---|---|---|
| (B) | | | |
| 1-(2-methyl-phenyl)-3-(1,2,3-thiadiazole-5-yl)-urea | = XVI | 50 | 10 |
| (A) | | | |
| N—(3,4-dichlorophenyl)-N',N'—dimethyl-urea | = II | 200 | 0 |
| | XVI + II | 10 + 10 | 10 |
| | | 25 + 25 | 26 |
| | | 40 + 40 | 40 |

EXAMPLE 9

Young cotton plants were treated as described in Example 8 and after several days the results were evaluated.

| Compound | | Amount of active agent in g/2.5 acres | Defoliation in % |
|---|---|---|---|
| (B) | | | |
| 1-methyl-1-phenyl-3-(1,2,3-thiadiazole-5-yl)-urea | = XVII | 50 | 5 |
| (A) | | | |
| N—(3,4-dichlorophenyl)-N',N'—dimethyl-urea | = II | 200 | 0 |
| | XVII + II | 10 + 10 | 15 |
| | | 20 + 30 | 40 |
| | | 40 + 10 | 50 |

EXAMPLE 10

Young cotton plants were treated as set out in Example 8 and the results determined three weeks later.

| Compound | | Amount of active agent in g/2.5 acres | Defoliation in % |
|---|---|---|---|
| (B) | | | |
| 1-(2-pyridyl)-3-(1,2,3-thiadiazole-5-yl)-urea | = XVIII | 50 | 70 |
| (A) | | | |
| N—(3,4-dichlorophenyl)-N',N'—dimethyl-urea | = II | 200 | 0 |
| | XVIII + II | 10 + 10 | 70 |
| | | 25 + 25 | 85 |

EXAMPLE 11

Young cotton plants were treated as described in Example 8 and the results evaluated several days later.

| Compound | | Amount of active agent in g/2.5 acres | Defoliation in % |
|---|---|---|---|
| (B) | | | |
| 4-methyl-1,2,3-thiadiazole-5-carboxylic acid-(cyclohexyl-methyl)-amide | = XIX | 50 | 15 |
| (A) | | | |
| N—(3,4-dichlorophenyl)-N',N'—dimethyl-urea | = II | 200 | 0 |
| | XIX + II | 10 + 10 | 35 |
| | | 40 + 10 | 45 |

EXAMPLE 12

Young cotton plants were treated by the procedure described in Example 8 and the results evaluated several days later.

| Compound | | Amount of active agent in g/2.5 acres | Defoliation in % | E (Colby) |
|---|---|---|---|---|
| (B) | | | | |
| d(+)-6-(α-methyl-benzylamino)-purine | = XXI | 20 | 25 | |
| (A) | | | | |
| N—(3,4-dichlorophenyl)-N',N'—dimethyl-urea | = II | 100 | 0 | |
| | XXI + II | 20 + 100 | 45 | (25) |

EXAMPLE 13

Young cotton plants were treated by the procedure described in Example 8 and the results evaluated several days later.

| Compound | | Amount of active agent in g/2.5 acres | Defoliation in % | E (Colby) |
|---|---|---|---|---|
| (B) | | | | |
| d(+)-6-(α-methyl-benzylamino)-purine | = XXI | 100 | 56 | |
| A | | | | |
| N—(3,4-dichlorophenyl)-N',N'—dimethyl-urea | = II | 200 | 0 | |
| | XXI + II | 50 + 50 | 67 | |

EXAMPLE 14

Young cotton plants having 6–8 evolved leaves were treated according to the procedure described in Example 1 and the results evaluated after 3 weeks had elapsed.

| Compound | | Amount of active agent in g/2.5 acres | Defoliation in % | E (Colby) |
|---|---|---|---|---|
| (B) | | | | |
| d(+)-6-(α-methyl-benzyl-amino)-purine | = XXI | 100 | 14 | |
| (A) | | | | |
| N—(3,4-dichlorophenyl)-N',N'—dimethyl-urea | = II | 300 | 0 | |
| N—(4-chlorophenyl)-N',N'—dimethyl-urea | = III | 300 | 0 | |
| N—phenyl-urea | = IV | 300 | 0 | |
| | XXI + II | 100 + 100 | 36 | (14) |
| | XXI + III | 100 + 100 | 29 | (14) |
| | XXI + IV | 100 + 100 | 39 | (14) |

EXAMPLE 15

Young cotton plants having germinated primary leaves were treated according to the procedure described in Example 1 and the results evaluated after 3 weeks had elapsed.

| Compound | | Amount of active agent in g/2.5 acres | Defoliation in % | E (Colby) |
|---|---|---|---|---|
| (B) | | | | |
| d(+)-6-(α-methyl-benzyl-amino)-purine | = XII | 100 | 8 | |
| 2,3-dihydro-5,6-dimethyl-1,4-dithiine-1,1,4,4-tetroxide | = XXII | 100 | 25 | |
| (A) | | | | |
| N—(3,4-dichloro-phenyl)-N',N'—dimethyl-urea | = II | 200 | 0 | |
| | XXI + II | 100 + 30 | 58 | (8) |
| | XXII + II | 100 + 30 | 67 | (25) |

EXAMPLE 16

Young bush bean plants having germinated primary leaves were treated as set out in Example 15 and the results obtained evaluated.

| Compound | | Amount of active agent in g/2.5 acres | Defoliation in % | E (Colby) |
|---|---|---|---|---|
| (B) | | | | |
| 2,3-dihydro-5,6-dimethyl-1,4-dithiine-1,1,4,4-tetroxide | = XXII | 100 | 17 | |
| (A) | | | | |
| N—(3,4-dichloro-phenyl)-N',N'—dimethyl-urea | = II | 100 | 0 | |
| | XXII + II | 100 + 100 | 41 | (17) |

EXAMPLE 17

Bush bean plants in the flower bud stage were treated as set out in Example 15 and the results evaluated after one and one-half weeks.

| Compound | | Amount of active agent in g/2.5 acres | Defoliation in % |
|---|---|---|---|
| (B) | | | |
| 2,3-dihydro-5,6-dimethyl-1,4-dithiine-1,1,4,4-tetroxide | = XXII | 150 | 81 |
| (A) | | | |
| N—(3,4-dichloro-phenyl)-N',N'—dimethyl-urea | = II | 200 | 0 |
| | XXII + II | 100 + 30 | 88 |

EXAMPLE 18

Heavily leaved colored nettle plants having a growth height of about 20–25 cm were treated with the following named compounds or their mixtures and the results of this treatment were evaluated 2 weeks later.

| Compound | | Amount of active agent in g/2.5 acres | Defoliation in % |
|---|---|---|---|
| (B) | | | |
| 2,3-dihydro-5,6-dimethyl-1,4-dithiine-1,1,4,4-tetroxide | = XXII | 200 | 12 |
| (A) | | | |
| N—(3,4-dichloro-phenyl)-N',N'—dimethyl-urea | = II | 200 | 0 |
| | XXII + II | 100 + 50 | 29 |

EXAMPLE 19

Young cotton plants having 6–8 evolved leaves were treated with the hereinafter set out compounds or their mixtures using the procedure described in Example 1 and the results obtained evaluated.

| Compound | | Amount of active agent in g/2.5 acres | Defoliation in % |
|---|---|---|---|
| (B) | | | |
| sodium chlorate | = XXII | 3000 | 7 |
| (A) | | | |
| N—(3,4-dichloro-phenyl)-N',N'—dimethyl-urea | = II | 300 | 0 |
| N—phenyl-urea | = IV | 300 | 0 |
| | XXII + II | 2900 + 100 | 39 |
| | XXII + IV | 2900 + 100 | 32 |

EXAMPLE 20

Young cotton plants having 6–8 evolved leaves were treated with the hereinafter set forth compounds or their mixtures according to the procedure of Example 1 and the results of the treatment evaluated after 1.5 weeks.

| Compound | | Amount of active agent in g/2.5 acres | Defoliation in % | E (Colby) |
|---|---|---|---|---|
| (B) | | | | |
| S,S,S—tributyl-phosphortrithioate | = XXIII | 300 | 37 | |
| (A) | | | | |
| N—(3,4-dichloro-phenyl)-N',N'—dimethyl-urea | = II | 300 | 0 | |
| N—(4-chloro-phenyl)-N',N'—dimethyl-urea | = III | 300 | 0 | |
| | XXIII + II | 300 + 100 | 59 | (37) |
| | XXIII + III | 300 + 100 | 48 | (37) |

EXAMPLE 21

Young cotton plants were treated with the hereinafter named compounds or their mixtures by the procedure described in Example 1 and the results evaluated several days later.

|  |  | Amount of active agent in g/2.5 acres | Defoliation in % | E (Colby) |
|---|---|---|---|---|
| Compound |  |  |  |  |
| (B) |  |  |  |  |
| 1,1'-dimethyl-4,4'-bipyridilium-dichloride | = XXIV | 100 | 54 |  |
| (A) |  |  |  |  |
| N—(4-chlorophenyl)-N',N'—dimethyl-urea | = III | 300 | 0 |  |
|  | XXIV + III | 100 + 100 | 71 | (54) |

EXAMPLE 22

Young cotton plants having 5 evolved leaves were treated according to the procedure of Example 1 and the results evaluated 3 weeks thereafter.

| Compound |  | Amount of active agent in g/2.5 acres | Defoliation in % | E (Colby) |
|---|---|---|---|---|
| B |  |  |  |  |
| N—phenyl-N'—(1,2,3-thiadiazole-5-yl)-urea | = I | 5 | 35 |  |
|  |  | 25 | 75 |  |
| (A) |  |  |  |  |
| N—(3-chloro-4-iodo-phenyl)-N'—methoxy-N'—methyl-urea | = XXV | 50 | 0 |  |
| N—phenyl-N'—cyclopropyl-urea | = XXVI | 50 | 0 |  |
| N—(3-fluorophenyl)-N'—cyclopropyl-urea | = XXVII | 50 | 0 |  |
| N—(3-chloro-4-fluorophenyl)-N'—cyclopropyl-urea | = XXVIII | 50 | 0 |  |
|  | I + XXV | 5 + 5 | 95 | (35) |
|  | I + XXVI | 5 + 5 | 85 | (35) |
|  | I + XXVII | 5 + 5 | 85 | (35) |
|  | I + XXVIII | 5 + 5 | 67 | (35) |

I claim:

1. A composition for defoliating cotton plants and having a synergistic effect comprising:
   (a) a compound of the Formula (I)

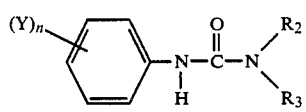

in which
- $R_2$ is hydrogen or $C_1$ to $C_4$ alkyl;
- $R_3$ is hydrogen, $C_1$ to $C_4$ alkyl, $C_1$ to $C_4$ alkoxy, or $C_3$ to $C_8$ cycloalkyl;
- Y can be the same or different and is hydrogen, halogen, $C_1$ to $C_4$ alkyl, $C_1$ to $C_4$ alkoxy, or trifluoromethyl; and
- n is the number 1 or 2;

in combination with
(b) a compound of the Formula (II)

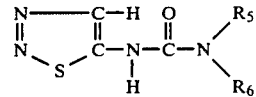

in which
- $R_5$ is hydrogen or $C_1$ to $C_4$ alkyl; and
- $R_6$ is phenyl, methylphenyl, or pyridyl;

wherein the weight ratio of compound of the Formula (I) to the compound of the Formula (II) is 1:1 to 10:1.

2. The composition for defoliating cotton plants and having a synergistic effect as defined in claim 1 wherein the compound of the Formula (II) is N-phenyl-N'-(1,2,3-thiadiazole-5-yl)-urea.

3. The composition for defoliating cotton plants and having a synergistic effect as defined in claim 1 comprising:
   ($a_1$) a compound of the Formula (I) selected from the group consisting of:
   (i) N-(4-chlorophenyl)-N',N'-dimethyl-urea;
   (ii) N-phenyl-urea;
   (iii) N-(4-isopropyl-phenyl)-N',N'-dimethyl-urea;
   (iv) N-(3-trifluoromethylphenyl)-N',N'-dimethyl-urea;
   (v) N-(3-chloro-4-methyl-phenyl)-N',N'-dimethyl-urea;
   (vi) N-(3-chloro-4-methoxy-phenyl)-N',N'-dimethyl-urea;
   (vii) N-(4-bromo-phenyl)-N'-methoxy-N'-methyl-urea; and
   (viii) N-phenyl-N',N'-dimethyl-urea; and
   ($b_1$) N-phenyl-N'-(1,2,3-thiadiazole-5-yl)-urea as the compound of the Formula (II), wherein the weight ratio between the compound of the Formula (I) to the compound of the Formula (II) is 5 to 1.

4. The composition for defoliating cotton plants and having a synergistic effect as defined in claim 1 comprising:
   ($a_1$) a compound of the Formula (I) selected from the group consisting of:
   (i) N-(3,4-dichlorophenyl)-N'-methoxy-N'-methyl-urea;
   (ii) N-(4-chlorophenyl)-N'-methoxy-N'-methyl-urea;
   (iii) N-(3,4-dichlorophenyl)-N'-methyl-N'-n-butyl-urea; and
   ($b_1$) N-phenyl-N'-(1,2,3-thiadiazole-5-yl)-urea as the compound of the Formula (II), wherein the weight ratio between the compound of the Formula (I) and the compound of the Formula (II) is 3 to 2.

5. The composition for defoliating cotton plants and having a synergistic effect as defined in claim 1 comprising:
   ($a_1$) a compound of the Formula (I) selected from the group consisting of:
   (i) N-(3-chloro-4-iodo-phenyl)-N'-methoxy-N'methyl-urea;
   (ii) N-phenyl-N'-cyclopropyl-urea;
   (iii) N-(3-fluorophenyl)-N'-cyclopropyl-urea; and
   (iv) N-(3-chloro-4-fluorophenyl)-N'-cyclopropyl-urea; and
   ($b_1$) N-phenyl-N'-(1,2,3-thiadiazole-5-yl)-urea as the compound of the Formula (II), wherein the weight ratio between the compound of the Formula (I) and the compound of the Formula (II) is 1 to 1.

6. The composition for defoliating cotton plants and having a synergistic effect as defined in claim 1 comprising:
   (a) N-(3,4-dichlorophenyl)-N',N'-dimethyl-urea as the compound of the Formula (I) and
   (b) N-phenyl-N'-(1,2,3-thiadiazole-5-yl)-urea as the compound of the Formula (II), wherein the weight ratio between the compound of the Formula (I) and the compound of the Formula (II) is 1:1 to 10:1.

7. The composition for defoliating cotton plants and having a synergistic effect as defined in claim 1 comprising:
   ($a_1$) a compound of the Formula (I) selected from the group consisting of:
   (i) N-(3,4-dichlorophenyl)-N',N'-dimethyl-urea;
   (ii) N-(3,4-dichlorophenyl)-N'-methoxy-N'-methyl-urea;
   (iii) N-(4-chlorophenyl)-N'-methoxy-N'-methyl-urea; and
   (iv) N-(3,4-dichlorophenyl)-N'-methyl-N'-n-butyl-urea;
   and
   ($b_1$) N-phenyl-N'-(1,2,3-thiadiazole-5-yl)-urea as the compound of the Formula (II), wherein the weight ratio between the compound of the Formula (I) and the compound of the Formula (II) is 3 to 2.

8. The composition for defoilating cotton plants and having a synergistic effect as defined in claim 1 comprising:
   ($a_1$) a compound of the Formula (I) selected from the group consisting of:
   (i) N-(3-chloro-4-iodophenyl)-N'-methoxy-N'methyl-urea;
   (ii) N-phenyl-N'-cyclopropyl-urea;
   (iii) N-(3-fluorophenyl)-N'-cyclopropyl-urea; and
   (iv) N-(3,4-dichlorophenyl)-N',N'-dimethyl-urea; and
   ($b_1$) N-phenly-N'-(1,2,3-thiadiazole-5-yl)-urea as the compound of the Formula (II), wherein the weight ratio between the compound of the Formula (I) and the compound of the Formula (II) is 1 to 1.

9. The composition for defoliating cotton plants and having a synergistic effect as defined in claim 1 comprising:
   (a) N-(3,4-dichlorophenyl)-N',N'-dimethyl-urea as the compound of the Formula (I); and
   (b) N-phenyl-N'-(1,2,3-thiadiazole-5-yl)-urea as the compound of the Formula (II), wherein the weight ratio between the compound of the Formula (I) and the compound of the Formula (II) is 2 to 1.

10. A composition for defoliating cotton plants and having a synergistic effect comprising:
    (a) a compound of the Formula (I) which is:
    (i) N-(3,4-dichlorophenyl)-N',N'-dimethyl-urea, or
    (ii) N-(4-chlorophenyl)-N',N'-dimethyl-urea; and
    (b) N-phenyl-N'-(1,2,3-thiadiazole-5-yl)-urea as the compound of the Formula (II), wherein the weight ratio between the compound of the Formula (I) and the compound of the Formula (II) is from 10:1 to 1:2.

11. The composition for defoliating cotton plants and having a synergistic effect as defined in claim 10 comprising:
    ($a_1$) a compound of the Formula (I) which is:
    (i) N-(3,4-dichlorophenyl-N',N'-dimethyl-urea, or
    (ii) N-(4-chlorophenyl)-N',N'-dimethyl-urea; and
    ($b_1$) N-phenyl-N'-(1,2,3thiadiazole-5-yl)-urea as the compound of the Formula (II), wherein the weight ratio between the compound of the Formula (I) and the compound of the Formula (II) is 1 to 2.

12. A method of defoliating cotton plants which comprises applying thereto in an amount of 10 to 1000 g/2.5 acres, the composition defined in claim 1.

13. A method of defoliating cotton plants which comprises applying thereto in an amount of 10 to 1000 g/2.5 acres, the composition defined in claim 9.

14. A method of defoliating cotton plants which comprises applying thereto in an amount of 10 to 1000 g/2.5 acres, the composition defined in claim 10.

15. A method of defoliating cotton plants which comprises applying thereto in an amount of 10 to 1000 g/2.5 acres, the composition defined in claim 11.

* * * * *